United States Patent

Rau

[11] Patent Number: 5,965,515
[45] Date of Patent: *Oct. 12, 1999

[54] COATED AMINE FUNCTIONALITY-CONTAINING MATERIALS

[75] Inventor: Allen H. Rau, Cincinnati, Ohio

[73] Assignees: The Andrew Jergens Company, Cincinnati, Ohio; Kao Corporation, Tokyo, Japan

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/522,926

[22] Filed: Sep. 1, 1995

Related U.S. Application Data

[63] Continuation of application No. 08/224,438, Apr. 7, 1994, Pat. No. 5,478,501.

[51] Int. Cl.[6] ............................... C11D 17/00; C11D 1/62
[52] U.S. Cl. ........................ 510/441; 510/135; 510/146; 510/151; 510/462; 510/470; 510/473; 510/474; 510/475; 510/499; 510/504; 510/509; 106/163.01; 106/206.1; 106/287.23; 424/466; 424/493; 424/494; 428/403; 428/407
[58] Field of Search ............................... 252/544, 174.13, 252/174.11, 174.23, 174.24, 174.14, 547, 132, DIG. 5; 106/287.23, 206.1, 163.01; 428/403, 407; 424/493, 494, 466; 514/957; 510/135, 146, 151, 441, 462, 475, 499, 504, 470, 473, 474, 509

[56] References Cited

U.S. PATENT DOCUMENTS

| | | | |
|---|---|---|---|
| 3,896,033 | 7/1975 | Grimm, III | 510/519 |
| 4,108,600 | 8/1978 | Wong | 8/137 |
| 4,339,335 | 7/1982 | Wixon | 510/441 |
| 4,545,784 | 10/1985 | Sanderson | 8/107 |
| 4,642,197 | 2/1987 | Kruse et al. | 510/298 |
| 4,664,817 | 5/1987 | Wixon | 510/441 |
| 4,732,765 | 3/1988 | Sasagawa et al. | 424/476 |
| 4,898,781 | 2/1990 | Onouchi et al. | 510/223 |
| 5,000,869 | 3/1991 | Dittert | 252/174.13 |
| 5,002,758 | 3/1991 | Ichii et al. | 424/44 |
| 5,110,603 | 5/1992 | Rau | 424/466 |
| 5,162,057 | 11/1992 | Akiyama et al. | 106/243 |
| 5,182,105 | 1/1993 | Takata et al. | 424/78.02 |
| 5,198,144 | 3/1993 | Ichii et al. | 252/174.11 |
| 5,411,746 | 5/1995 | Signorino et al. | 424/464 |

FOREIGN PATENT DOCUMENTS

| | | |
|---|---|---|
| 0063512 | 10/1982 | European Pat. Off. . |
| 3236375 | 4/1984 | Germany . |
| 56-053299 | 5/1981 | Japan . |
| 58-186693 | 10/1983 | Japan . |
| 59-024800 | 2/1984 | Japan . |
| 61-272298 | 12/1986 | Japan . |
| 64-001795 | 1/1989 | Japan . |
| 05131742 | 5/1993 | Japan . |

*Primary Examiner*—Lorna M. Douyon
*Attorney, Agent, or Firm*—Long Aldridge & Norman LLP; Steven B. Kelber

[57] ABSTRACT

Amine functionality-containing materials such as cationic cellulose-based compositions are coated to suppress their tendency to generate "amine odors" in an alkaline pH environment. Further provided are effervescent compositions, liquid or solid soap formulations, fabric softeners, shampoos and the like comprising such materials coated with a suitable coating composition.

14 Claims, 2 Drawing Sheets

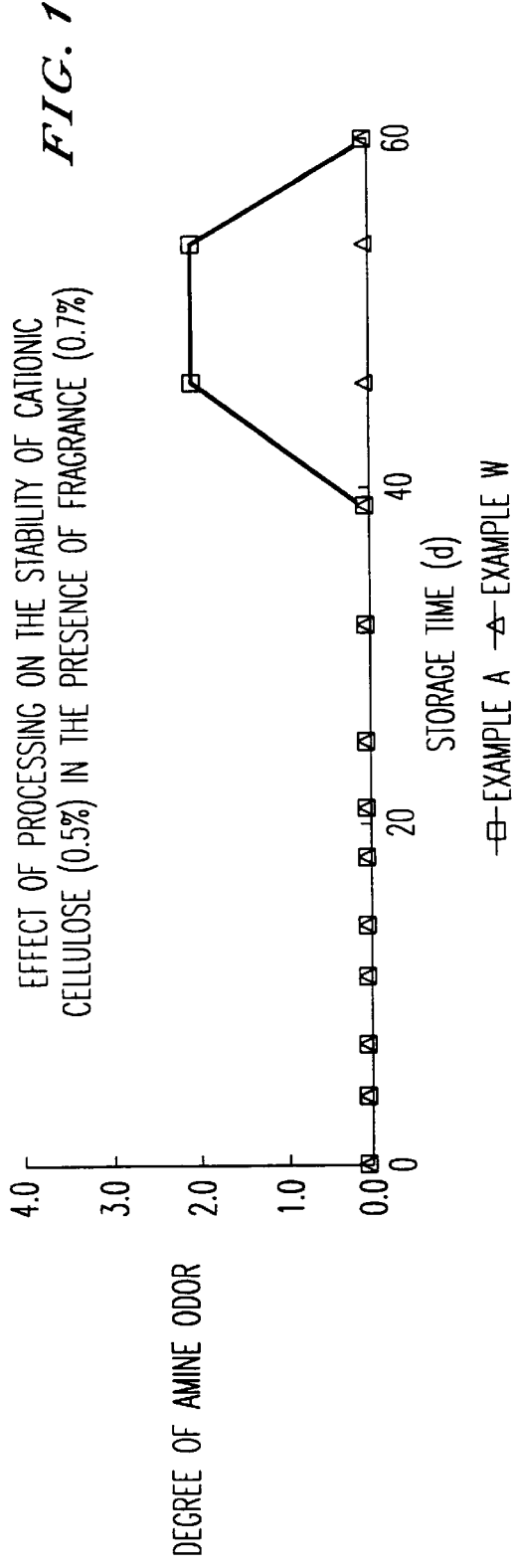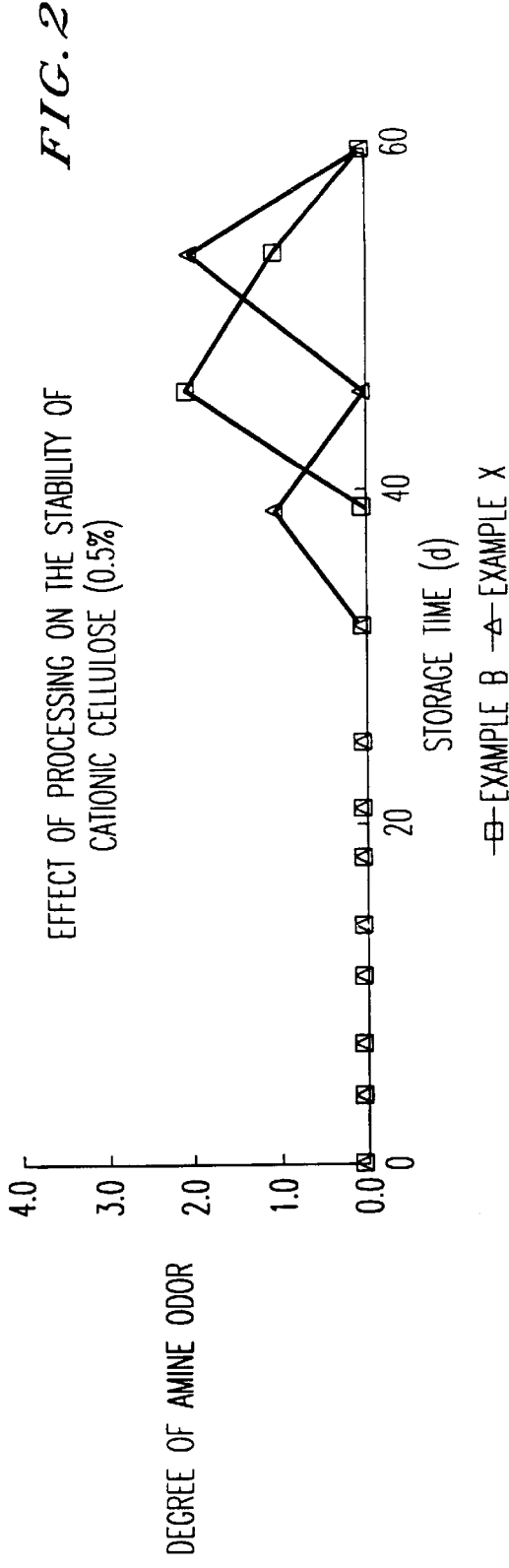

COATED AMINE FUNCTIONALITY-CONTAINING MATERIALS

This is a Continuation of application Ser. No. 08/224,438 filed on Apr. 7, 1994, now U.S Pat. No. 5,478,501.

BACKGROUND OF THE INVENTION

1. Field of the Invention

This invention relates to compositions comprising amine functionality-containing materials provided with a coating which suppresses the generation and release of offensive "amine" odors. The compositions of the present invention allow for a delay of the onset of amine odors, and also greatly reduce the intensity of amine odors.

2. Discussion of the Background

Amine functionality-containing materials are commonly used in cosmetic and household products, including bathing preparations. Many products containing materials with amine functionalities (quaternary ammonium and amide moieties as well as materials with trace or greater quantities of amine) such as some liquid and solid soap, are used in everyday life. Other amine functionality-containing products include bath preparations such as bubble bath and bath powders and beads, and effervescent tablet compositions such as ActiBath®. Cationic cellulose, a quaternary ammonium-containing product, is one example of an amine functionality-containing material that is frequently included in such compositions due to the high quality "feel" or slipperiness it lends the product. The inclusion of cationic cellulose (polyquaternium 10, Polymer JR, Polymer LR, etc.) in products that are either alkaline in nature or used at an alkaline pH, generates amine-based volatile products.

A problem with the above products that are a part of our daily lives, is that the amine functionality-containing materials which ordinarily comprise these products release amine odors, commonly characterized by consumers as a "fishy" smell in an alkaline environment. These amine odors are formed as a result of the amine functionality-containing material coming into contact with alkaline materials for an extended period of time. At a neutral or low pH, amine salts are formed. These salts are not volatile and therefore non-odorous. However, in a high pH environment (above pH≈7.5), the amine odor surfaces and is unavoidable. These amine odors are very unpleasant and represent a significant problem, especially for products which are formulated without fragrances.

One way to control these odors is to decrease the level of the amine functionality-containing materials. However, the product produced having a lower concentration of these materials is normally not as effective or desirable.

Other efforts to control the amine odor have been attempted. For example, U.S. Pat. No. 5,211,870 to Gilbert et al describes the use of a zeolite odor-controlling agent comprising a member selected from the group consisting of intermediate ($SiO_2/Al_2O_3$)Y zeolites, mordenites, large pore beta zeolites, and mixtures thereof, in combination with a personal cleansing bar or in liquid cleansing compositions.

U.S. Pat. No. 5,204,023 to Behan et al discloses the use of reaction products of amines and aldehydes with the potential to chemically reduce the concentration of aldehydic malodorance by direct chemical trapping, with concomitant release of desirable perfume aldehydes into the product over time. The process, in effect, provides an exchange process by replacing unwanted aldehydes with desirable aldehydes.

U.S. Pat. No. 5,002,758 to Ichii et al (hereinafter, "Ichii '758") discusses a bathing preparation containing fumaric acid and a carbonate which does not cause floating of fumaric acid or foaming of a bath. The process provides for the mixing of a particulate material with another substance that will melt at a much lower temperature than the particulate material. Specifically, the bathing preparation is obtained by incorporating into the fumaric acid bathing preparation, or as a coating thereof, a specific amount of carboxymethyl cellulose or an alkali metal salt thereof or polyethylene glycol, and a nonionic surface active agent.

However, a satisfactory amine functionality-containing material which delays the onset of amine odors for an extended period of time and which also reduces the intensity of the amine odor has not been developed to date.

SUMMARY OF THE INVENTION

Accordingly, it is an object of the present invention to provide amine functionality-containing material which allows for a delay of the onset of the production of amine malodors and which also allows for a reduction in the intensity of the amine malodor even in alkaline pH.

The above objects have been met by the present invention which provides compositions comprising amine functionality-containing cationic cellulose materials coated with a suitable coating material. The present compositions allow for a delay of the onset of amine malodors for a sufficiently extended period of time and concurrently, allow for a significant decrease in the intensity of the amine odor.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a graph of degree of amine odor versus storage time and illustrates the effect of processing on the stability of cationic cellulose in the presence of a fragrance. The graph compares Comparative Example A with Inventive Example W of the present invention;

FIG. 2 is a graph of degree of amine odor versus storage time, and illustrates the effect of processing on the stability of cationic cellulose. The graph compares Comparative Example B with Inventive Example X of the present invention;

DETAILED DESCRIPTION OF THE INVENTION

Figure 3:
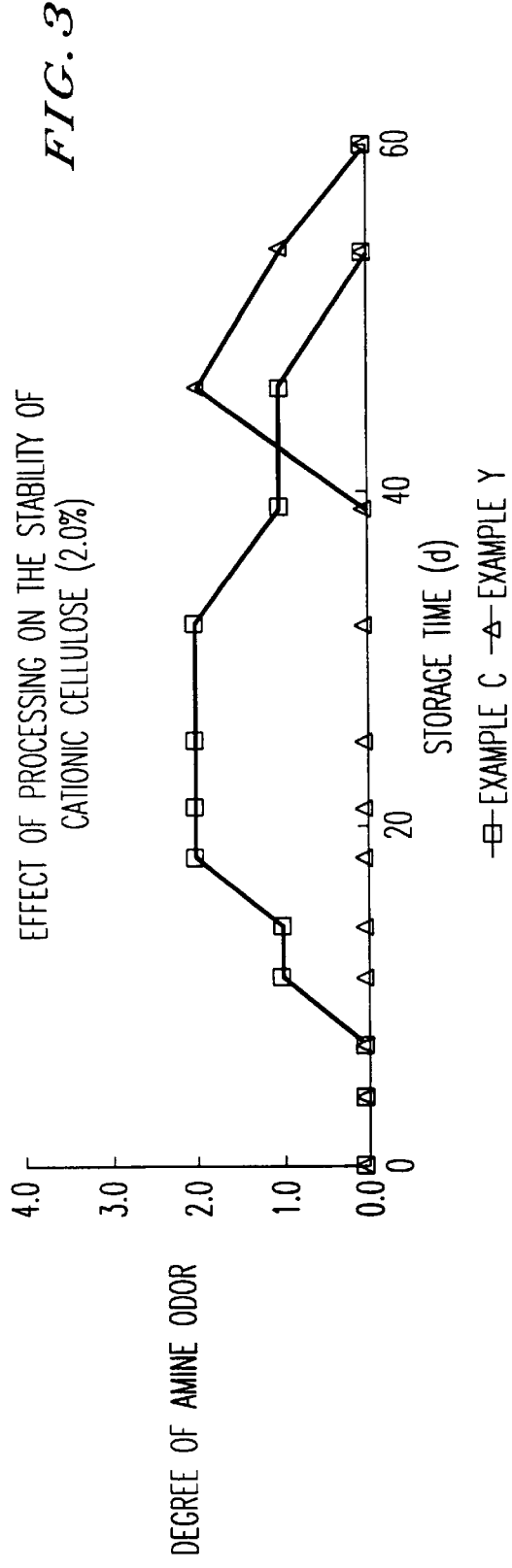
FIG. 3 is a graph of degree of amine odor versus storage time, and illustrates the effect of processing on the stability of cationic cellulose. The graph compares Comparative Example C with Inventive Example Y of the present invention.

The present invention will now be described more fully hereinafter with references to the accompanying drawings, in which preferred embodiments of the invention are shown. This invention can, however, be embodied in many different forms and should not be construed as limited to the embodiments set forth herein; rather, Applicant provides these embodiments so that this disclosure will be thorough and complete, and will fully convey the scope of the invention to those skilled in the art. One exemplary product that benefits from the coating described in this application is the effervescent bathing product disclosed and claimed in U.S. Pat. No. 5,110,603. This material, which advantageously includes a colloidal material like colloidal oatmeal, can be improved through this invention. The entire disclosure of U.S. Pat. No. 5,110,603 is incorporated-herein-by reference.

The compositions useful in the present invention comprise amine functionality-containing compound and material. This includes materials which in the presence of alkaline agents such as OH⁻ ions, generate free amines. Exemplary materials include molecules with quaternary ammonium groups, wherein at least one of the substituents on the nitrogen molecule is an alkyl group of at least two carbon atoms, which will generate amines through Hoffman elimination reactions in the presence of alkaline materials or alkaline environments. Additionally, amides of the formula:

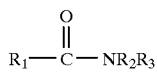

generate amines under alkaline conditions, e.g., hydrolysis via nucleophilic attack. Additionally, many compounds are prepared with amine impurities. Given the strength of "amine odors", even trace contaminants of amine may be undesirable, when released under use or storage conditions. A preferred amine functionality-containing material within the scope of this invention is cationic cellulose coated with a suitable coating composition. Other amine functionality-containing materials include cationic guar and other polymers with quaternary ammonium groups, long chain amides such as mono- and di-ethanol fatty amides, cationic surfactants with quaternary ammonium moieties (e.g,. dialkyl dimethyl ammonium chloride), imidazolinium compounds, amphoteric compounds with amine or amide moieties such as betaines, sarcosinates, etc. and the like. The coating of the amine functionality containing material physically isolates the substance, such as cationic cellulose and delays the generation of amine odor, even in environments where the pH is above approximately 7.5.

The amine functionality containing material useful in the present invention is normally solid at room temperature. As cationic cellulose, it may be present in the compositions in an amount of from about 0.01 to 10% based on the weight of the total composition, preferably about 0.05 to 5% by weight.

The coating composition of the present invention can be any coating material that is not reactive with the amine functionality-containing material or the surrounding environment, and which has a melting point lower than that of cationic cellulose or other amine functionality containing material. Examples include long chain nonionic surfactants free of amine functionalities, water soluble polymers, waxes and oils. Among nonionic surfactants, long chain compounds are preferably employed such as glyceryl fatty acid esters, propylene glycol fatty acid esters, sorbitan fatty acid esters, polyoxyethylene sorbitan fatty acid esters, tetraoleic acid polyoxyethylene sorbitol, polyoxyalkylene polyethers, polyoxyethylene alkyl ethers, polyoxyethylene polyoxypropylene glycol, polyoxyethylene polyoxypropylene alkyl ethers, polyethylene glycol fatty acid esters, polyoxyethylene castor oil, polyoxyethylene hardened castor oil, polyglycerol fatty acid esters, and mixtures thereof. Polyoxyalkylene polyethers are preferred.

Water soluble polymers such as polyethyleneglycol (PEG), polyvinyl alcohol (PVA) and polyvinyl pyrrolidone (PVP) as well as polysaccharides, simple sugars, starches, natural sums and cellulose derivatives like (hydroxyethyl) or (hydroxypropyl) cellulose are acceptable coating materials within this invention. Particularly preferred are polyethylene glycol (PEG), polypropylene glycol (PPG), and mixtures thereof.

Other suitable coating materials include waxes and oils such as those based on hydrocarbon waxes, silicone waxes, triglyceride waxes. Other suitable compounds include plant sterols, as well as alkyl/alcohol esters such as myristyl myristate, stearyl palmitate and other esters of long chain carboxylic groups and long chain alcohols.

It should be noted that the coating material that is selected must be effectively removed by use in its intended environment. Thus, coatings that are soluble in aqueous mediums or which melt in the intended use environment such as a hot bath or clothes dryer, are preferred.

The coating materials should be selected so as to ensure that the melting point of the coating component is lower than that of the amine functionality-containing material. Where the coating material comprises PEG as a component, and the amine functionality-containing material is cationic cellulose, it is desirable that the molecular weight of the PEG be between about 5000–10,000 (weight average). Thus, whether the coating component is a long chain nonionic material, a wax, a fatty alcohol, or a combination thereof, the ingredients are selected, and molecular weight controlled, so as to provide for a coating material that exhibits an overall melting point lower than that of the material to be coated. In an alternative, a suitable coating can be prepared as a solution with a low boiling point or easily extracted solvent. The coating solution is sprayed onto the material to be coated, with evaporation of the solvent. Polyvinyl alcohol may be dissolved in ethanol and spray coated onto the target material, with ethanol evaporization, as one example of this alternative.

The amount of coating material used will depend on the amount of material to be coated and its particle size. Frequently, the composition that is to be coated is mixed or compounded after coating with at least an alkaline element, and a variety of other solid materials. Where only the amine functionality-containing material is to be coated, the coating material will be present in a-minimum amount. The invention contemplates, as well, coating all materials together, save for the materials exhibiting an alkaline pH. Thus, the coating material in this situation would be present, on the basis of the total weight of the coated composition, at a maximum. The amount of coating material to be used will also be determined by the nature of the product to be coated. Thus, where the material to be coated includes fine-grained material, or material with a large surface area, a relatively greater amount of coating material will be used. As a general, but non-limiting guideline, the amount of coating material in the coated composition will vary from about 2 percent–50 percent, by weight.

Further compounds which can be used in the present invention, either in combination with the precoated amine functionality-containing material such as cationic cellulose or in combination with the cationic cellulose to be coated, include an organic acid and acidic salt thereof such as citric acid, succinic acid, malic acid, tartaric acid, fumaric acid, malonic acid, pyridone carboxylic acid, adipic acid, benzoic acid, sodium citrate, sodium succinate, sodium fumarate, sodium adipate, etc. Inorganic acids (and their salts) may also be used in the practice of this invention, including phosphoric acid, acidic sodium hexametaphosphate, acidic sodium pyrophosphate, sulfamic acid, etc. These organic acids can be used alone or in combinations of two or more. Fumaric acid is preferred and is less expensive than conventionally employed organic acids, e.g., citric acid, succinic acid, malic acid and tartaric acid. The total organic acid content falls within a range of about 5–80%, preferably 10–50%.

A sucrose fatty acid ester such as sucrose stearate can be used either in combination with the precoated cationic cellulose or in combination with the cationic cellulose to be coated. The sucrose fatty acid ester is present in an amount of about 0.001–0.27%, and preferably 0.01–0.017%.

Carbonate salts can also be used in the amine functionality-containing coated composition of the present invention especially when preparing bathing preparations such as ActiBath®, bubble bath, bath crystals, bath powder and the like. Examples include sodium carbonate, sodium bicarbonate, potassium hydrogencarbonate, potassium carbonate, calcium carbonate, magnesium, carbonate, and sodium sesquicarbonate. These carbonates can be used either individually or in combinations of two or more thereof. The carbonates, when used, are of course added to the composition after coating of the amine functionality-containing material is completed. The coating forms a barrier between the material and the (alkaline) carbonate. The carbonates are present in an amount of 5–80%, 10–50% on a preferred basis.

As noted, certain preparations, such as that of U.S. Pat. 5,110,603 include additional solid materials such as colloidal oatmeal, which can also constitute part of the coated material.

The amine functionality-containing composition of the present invention as a bathing preparation can further comprise additional ingredients including cosmetic oils such as mineral oil, petrolatum, fatty acid esters, silicone oils and triglyceride oils; fillers such as dextrins, starches and sugars (glucose, fructose, mannose, etc.); fragrances; inorganic acids; such as boric acid, methasilicic acid, silicic anhydride, etc.; vitamins such as Vitamins A, C, D, E, etc; crude drugs such as fennel, philodendron bark, matricaria, cinnamon bark, safflower, paeoniae radix, ginger, calamus, cnidium rhizome, angericae radix, aurantii nobilis pericarpium, atractylodes lancea rhizoma, Japanese valerian rhizome, angelicae dahuricae radix, bitter orange peel, mentha herb, hoelen, ginseng, etc.; artificial dyes such as synthetic dyes, etc.; natural dyes such as chlorophyll, riboflavin, crocin, safflower, anthraquinone, etc.; cosmetic powders such as acrylic resins, styrene resins, epoxy resins, nylon, polyethylene, polypropylene, polyvinyl chloride, polyethylene terephthalate resins and polytetrafluoroethane, copolymers thereof, silicic acid, calcium silicate, natural aluminum silicate, synthetic aluminum silicate, zeolite, titanium oxide, talc, kaoline, mica, bentonite, etc.; and other materials such as sulfur, hot spring deposit, fine sand, mica, neutral clay, roasted rice bran, bactericides, sea weed extracts, proteolytic enzymes, silicones and preservatives.

The amounts of these additional ingredients vary depending on the desired effect and desired formulation and are not critical to the present invention.

The amine functionality-containing compositions of the present invention are prepared by heating a mixture of, e.g., cationic cellulose with the coating composition which will melt at a lower temperature than the cationic cellulose. The process is carried out in such a way that the mixture is heated above the melting point of the coating composition, but below that of the cationic cellulose or other amine functionality containing material. The melted coating material spreads over the cationic cellulose, the coating material solidifies over the amine-forming cationic cellulose, thereby forming an inert film over the cationic cellulose.

This inert film serves to insulate the amine functionality-containing material from alkaline materials, present in both the overall composition (e.g., carbonate salts) and alkaline local environments (e.g., storage conditions) prior to use.

The heat can be added by using a jacketed mixing vessel and appropriate heat source. Alternatively, a mixer in which high shearing action of the blades generates sufficient heat to melt the coating material can be used. As previously noted, the coating, in a low boiling point or extractable solvent, can be spray coated on, followed by evaporation or extraction of the solvent.

Other details of coating the amine functionality-containing material of the present invention can be found in U.S. Pat. No. 5,002,758 (Ichii et al) which describes the coating of fumaric acids and/or organic acids with carboxymethlycellulose or a metal salt thereof or PEG. U.S. Pat. No. 5,002,758 is herein incorporated by reference.

The coated cationic cellulose can then be mixed with other suitable materials listed above such as carbonate salts, cosmetic oils, organic acids, fillers, fragrances, inorganic acids, vitamins, crude drugs, natural dyes, artificial dyes, pigments, cosmetic powders, and/or any other suitable ingredients. In the alternative, non-alkaline components (e.g., other than carbonate salts) may be mixed with the amine functionality-containing materials and then coated in mass.

The resulting coated particulates are sufficiently isolated from any alkaline materials that may be present in order to prolong the formation of undesirable amine odors for an extended period of time.

The final form of the amine functionality containing composition of the present invention includes tablets such as the currently marketed effervescent tablet ActiBath®; powders such as bath powders, granules such as bath beads; solid materials such as bar soap formulations; fabric softeners in combination laundry detergent/fabric softener products, suspensions and emulsions such as bubble bath, foaming milk bath, bath oils, shampoos and conditioners, etc. When prepared in the form of a soap or detergent, anionic surfactants and/or amphoteric surfactants are commonly employed.

Particularly, the present invention is useful for substantially decreasing amine odors from bar soap formulations which are generally quite caustic (pH=9–11).

As stated above, the present invention can be used with ActiBath®. In this case, coated fumaric acid is used in combination with sodium carbonate and sodium bicarbonate. The levels of the materials which produce amine odors can be substantially increased in spite of the alkalinity of the carbonate salts which normally cause malodors to be formed. Further, the onset of amine odor is delayed for a sufficiently extended period of time.

The following data employing cationic cellulose as the amine functionality-containing material demonstrates that the present compositions comprising such material coated with a coating material allow for a substantial delay of the release of amine odors that can be formed when the amine functionality-containing composition is in contact with alkaline materials for an extended period of time. Specifically, the formulas containing cationic cellulose coated with a suitable coating composition are stable against the development of amine malodors much longer than identical formulas in which the cationic cellulose has not been coated. This increase in stability is demonstrated by the fact that formulas that used uncoated cationic material released detectable levels of amine after 7 to 11 days of storage at 50° C. On the other hand, formulas which contained coated material did not begin to release the amine until at least 39 days of storage at elevated temperatures. Additionally, the intensity of the amine malodor was lower with the coated material of the present invention.

The invention will be further explained in the following examples. However, the examples are for purposes of illustration only, and are not intended to limit the scope of the subject matter of the present invention. In the examples, Examples W–Z reflect the invention of this application. They are compared with Comparative Examples A–D which include uncoated cationic cellulose, and thus are outside the scope of this invention.

EXAMPLES

Preparation of coated nitrogen-containing effervescent tablets.

Effervescent tablet compositions were prepared with 3 levels of cationic cellulose i.e., 0.5%, 2.0% and 5.0% (Table 1). The 0.5% cationic cellulose samples were made both with and without fragrance (Comparative Example A and Inventive Comparative Example W of Table 1 were made with fragrance, whereas Example B and Comparative Example X were formulated without fragrance). The amine functionality-containing cationic cellulose material was included either in the coating mix or in the final mix (Examples A–D contain cationic cellulose in the final mix, whereas Inventive Examples W–Z of the present invention contain cationic cellulose in the coating mix). Exact formulas are shown in Table I.

The coating process was carried out according to the method described in Example 2 of U.S. Pat. No. 5,002,758. Fumaric acid, PEG-150, sucrose stearate, and in appropriate cases, amine functionality-containing cationic cellulose (CTFA name: polyquaternium 10) were mixed using high shear until the product temperature reached 65° C. An amount of 7.3% PEG-150 (based on the total weight of all powders) was used in each case. The resulting mixtures were cooled while stirring to achieve the surface coating.

The coated acid and cationic cellulose particles were mixed with the remaining raw materials. Tablets were compressed at 10–15 tons of pressure using a conventional mechanical tablet press.

TABLE I

|  | Comparative Example | | | | Inventive Example | | | |
| --- | --- | --- | --- | --- | --- | --- | --- | --- |
|  | A | B | C | D | W | X | Y | Z |
| Coating Mix: | | | | | | | | |
| Fumaric Acid | 36.98 | 36.98 | 36.42 | 35.30 | 36.96 | 36.96 | 36.36 | 35.16 |
| Sucrose Stearate | 0.02 | 0.02 | 0.02 | 0.02 | 0.02 | 0.02 | 0.02 | 0.02 |
| PEG | 2.96 | 2.96 | 2.92 | 2.83 | 3.00 | 3.00 | 3.07 | 3.21 |
| Cationic Cellulose | — | — | — | — | 0.50 | 0.50 | 2.00 | 5.00 |
| Final Mix: | | | | | | | | |
| Coating Mix from Above | 39.96 | 39.96 | 39.35 | 38.15 | 40.48 | 40.48 | 41.45 | 43.39 |
| Sodium Carbonate | 18.05 | 18.05 | 17.78 | 17.24 | 18.04 | 18.04 | 17.75 | 17.16 |
| Sodium Bicarbonate | 18.38 | 18.38 | 18.10 | 17.55 | 18.37 | 18.37 | 18.07 | 17.47 |
| Mineral Oil | 2.60 | 3.30 | 3.25 | 3.15 | 2.60 | 3.30 | 3.25 | 3.14 |
| Oleth-9 | 0.76 | 0.76 | 0.75 | 0.73 | 0.76 | 0.76 | 0.75 | 0.72 |
| Sorbitol | 5.08 | 5.08 | 5.01 | 4.85 | 5.08 | 5.08 | 5.00 | 4.83 |
| Dextrin | 9.90 | 9.90 | 9.75 | 9.45 | 9.90 | 9.90 | 9.74 | 9.41 |
| Titanium Dioxide | 4.07 | 4.07 | 4.00 | 3.88 | 4.08 | 4.06 | 4.00 | 3.97 |
| Fragrance | 0.70 | — | — | — | 0.70 | — | — | — |
| Cationic Cellulose | 0.50 | 0.50 | 2.00 | 5.00 | — | — | — | — |
| Total Sum: | 100.00 | 100.00 | 100.00 | 100.00 | 100.00 | 100.00 | 100.00 | 100.00 |

Evaluation of amine odors produced upon aging of tablets.

Tablets were sealed in moisture-proof foil wrappers and placed in a 50° C. oven to accelerate the effects of aging. It is assumed that one month at this elevated temperature is equivalent to 1.5–2 years at normal ambient conditions. Every few days, a sample tablet, chosen at random, from each example formulation was removed from the oven, cooled to room temperature, and unsealed for odor evaluation. The odor evaluation was done by a professional fragrance evaluator who was unaware of the identity of the tested materials (the test was blind) using the following scale:

0: no change

1: very slight change (amine odor is barely perceptible)

2: slight change (slight amine odor is noticeable)

3: change (unacceptable amine odor is easily noticeable).

Additionally, fragrance stability was checked in the tablets which included fragrance oil. This assessment (whether the fragrance character had changed or not) was also performed by the professional fragrance evaluator.

Following the evaluation, the samples were resealed and placed back in the oven. The once-opened tablets were marked so that they could not be chosen for the next evaluation. This allowed evaluation of undisturbed tablets at each study point.

Data from all of the fragrance evaluations is presented in Tables II and III below and in FIGS. I–IV.

TABLE II

Presence of Amine Odor from Example Formulations

| Example | Days of storage @ 50° C. | | | | | | | | | | | | |
|---|---|---|---|---|---|---|---|---|---|---|---|---|---|
| | 0 | 4 | 7 | 11 | 14 | 18 | 21 | 25 | 32 | 39 | 46 | 54 | 60 |
| A | 0 | 0 | 0 | 0 | 0 | 0 | 0 | 0 | 0 | 0 | 2 | 2 | 0 |
| B | 0 | 0 | 0 | 0 | 0 | 0 | 0 | 0 | 0 | 0 | 2 | 1 | 0 |
| C | 0 | 0 | 0 | 1 | 1 | 2 | 2 | 2 | 2 | 1 | 1 | 0 | 0 |
| D | 0 | 0 | 1 | 0 | 3 | 3 | 3 | 3 | 2 | 1 | 1 | 0 | |
| W | 0 | 0 | 0 | 0 | 0 | 0 | 0 | 0 | 0 | 0 | 0 | 0 | 0 |
| X | 0 | 0 | 0 | 0 | 0 | 0 | 0 | 0 | 1 | 0 | 2 | 0 | |
| Y | 0 | 0 | 0 | 0 | 0 | 0 | 0 | 0 | — | 2 | 1 | 0 | |
| Z | 0 | 0 | 0 | 0 | 0 | 0 | 0 | 0 | 2 | 3 | 2 | 0 | |

TABLE III

Quality of Fragrance in Example Formulations

| Example | Days of storage @ 50° C. | | | | | | | | | | | | |
|---|---|---|---|---|---|---|---|---|---|---|---|---|---|
| | 0 | 4 | 7 | 11 | 14 | 18 | 21 | 25 | 32 | 39 | 46 | 54 | 60 |
| A | – | – | – | – | – | – | – | – | – | – | + | + | + |
| W | – | – | – | – | – | – | – | – | – | – | – | – | – |

Key:
–: No change in fragrance character
+: Change in fragrance character

The data clearly shows that coating the cationic cellulose dramatically delays and reduces the intensity of amine malodor formation that is common when quaternary nitrogen-containing compounds are subjected to alkaline environments. The result is that higher levels of these compounds can be used in alkaline products without the risk of offending consumers with undesirable malodors. The current typical percentages of these materials in cosmetic products, which range from 0.05% to 2%, may now be increased to higher levels by using this technology.

Even when cationic cellulose is included at a low level (0.5%), the amine odor that is generated over time when this material is uncoated is not masked by a conventional cosmetic fragrance. However, when the cationic cellulose is coated, there is no detectable amine odor even after 2 months of storage at 50° C. Also unexpectedly, the professional fragrance evaluator noted, as shown in Table III, that the fragrance remained more stable in the tablets that contained the coated cationic cellulose than in the products where this material was left uncoated.

Figure 4:
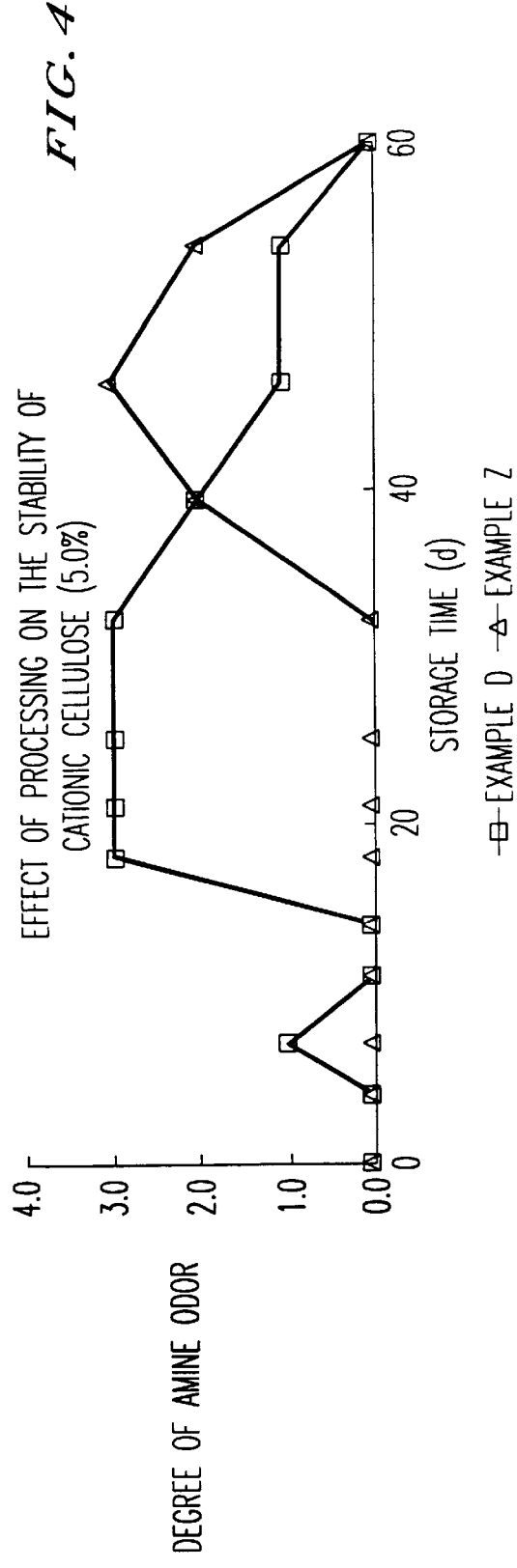
FIG. 4 is a graph of degree of amine odor versus storage time, and illustrates the effect of processing on the stability of cationic cellulose. The graph compares Comparative Example D with Inventive Example Z of the present invention.

Detailed examination of the data indicates that, whether or not the amine functionality-containing material is coated or not, the amine odor reaches a maximum and then decreases to non-detectable levels (FIGS. 1–4). This is because each tablet contains only a finite amount of quaternary nitrogen that can be converted to amine. Once this material has reacted, no additional amine can be generated.

The following claims are not designed to limit the scope of the subject matter of the present invention. Applicants have endeavored to illustrate their invention by extensive embodiment of possible combinations. Nonetheless, it is recognized that the possible combinations are endless, and cannot be exhaustively embodied. Given the above teaching, those of ordinary skill in the art will arrive at enhancement agents and additives not specifically exemplified in the foregoing application. The examples are not intended to be limiting, and the identification of other combinations, given the foregoing disclosure, is well within the skill of those practicing this technology without undue experimentation. Such combinations are intended to be within the scope of the invention, save as expressly limited or excluded by the claims set forth below.

What is claimed as new and is desired to be secured by Letters Patent of the United States is:

1. A coated amine functionality-containing composition comprising 0.01–10% by weight, based on the total weight of the composition, a polymer comprising quaternary ammonium groups, said polymer in particulate form being coated with a water-soluble coating composition comprising at least one water-soluble coating agent selected from the group consisting of water-soluble long chain non-ionic surfactants free of amine functionalities, water-soluble polymers selected from the group consisting of polyethyleneglycol, polypropyleneglycol, polyvinylpyrrolidone, polysaccharides, starches, gums, hydroxyethyl cellulose, hydroxypropyl cellulose and mixtures thereof, and wherein said water-soluble coating composition has a melting point lower than that of said polymer comprising quaternary ammonium groups the composition further comprising at least one other suitable material selected from the group consisting of carbonate salts, cosmetic oils, organic acids, fillers, fragrances, inorganic acids, vitamins, crude drugs, natural dyes, artificial dyes, pigments and cosmetic powders.

2. The coated composition of claim 1, wherein said polymer comprising quaternary ammonium group is present in an amount of about 0.05 to 5% by weight.

3. The coated composition of claim 1, wherein said suitable material is a fragrance.

4. The coated composition of claim 1, wherein said coating composition is (1) soluble in the environment in which it is to be used and insoluble in ambient storage conditions or (2) melts at a temperature above that of ambient storage conditions and no higher than conditions of use.

5. The coated composition of claim 1, wherein said polymer is cationic cellulose.

6. The coated composition of claim 1, wherein said coated composition is in the form of an effervescent preparation, said preparation further comprising 5–80% by weight carbonate salt, which carbonate salt is, prior to use, isolated from said polymer comprising quaternary ammonium groups by said coating composition.

7. The coated composition of claim 6, wherein said coating agent is selected from the group consisting of polyethylene glycol, polypropylene glycol and mixtures thereof.

8. The coated composition of claim 6, wherein said coating agent is polyethylene glycol.

9. The coated composition of claim 6, wherein said polymer comprising quaternary ammonium groups is present in an amount of 0.05–5% by weight.

10. The coated composition of claim 6, wherein said polymer comprising quaternary ammonium groups comprises cationic cellulose.

11. The coated composition of claim 6, wherein said coated composition further comprises a colloidal material selected from the group consisting of colloidal oatmeal, corn flour, wheat flour, soy flour, rice flour, barley flour, cornmeal, almond meal, hydrophobic starch, water-insoluble gum, cellulose and mixtures thereof.

12. The coated composition of claim 11, wherein said colloidal material is coated together with said polymer comprising quaternary ammonium groups.

13. The coated composition of claim 6, wherein said suitable material is a fragrance.

14. The coated composition of claim 1, wherein said composition is in the form of a soap or detergent formulation.

* * * * *